US012697034B2

(12) United States Patent
Stender et al.

(10) Patent No.: US 12,697,034 B2
(45) Date of Patent: Aug. 4, 2026

(54) MEDICAL DEVICE FOR EVALUATING A PULSATILE SIGNAL

(71) Applicants: Drägerwerk AG & Co. KGaA, Lübeck (DE); Karlsruher Institut für Technologie, Karlsruhe (DE)

(72) Inventors: Birgit Stender, Lübeck (DE); Michael Kircher, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 1181 days.

(21) Appl. No.: 17/480,613

(22) Filed: Sep. 21, 2021

(65) Prior Publication Data

US 2022/0087543 A1    Mar. 24, 2022

(30) Foreign Application Priority Data

Sep. 22, 2020    (DE) ..................... 10 2020 124 582.3

(51) Int. Cl.
| | |
|---|---|
| *A61B 5/02* | (2006.01) |
| *A61B 5/021* | (2006.01) |
| *A61B 5/029* | (2006.01) |

(52) U.S. Cl.
CPC ...... *A61B 5/02007* (2013.01); *A61B 5/02108* (2013.01); *A61B 5/029* (2013.01)

(58) Field of Classification Search
CPC . A61B 5/02007; A61B 5/02108; A61B 5/029; A61B 5/021; A61B 5/02028; A61B 5/022
USPC ................ 600/485, 486, 488, 481, 483, 484
See application file for complete search history.

(56) References Cited

U.S. PATENT DOCUMENTS

| | | | | |
|---|---|---|---|---|
| 5,390,679 A | * | 2/1995 | Martin | A61B 5/029 |
| | | | | 600/526 |
| 5,423,323 A | * | 6/1995 | Orth | A61B 5/0215 |
| | | | | 600/481 |
| 6,485,431 B1 | * | 11/2002 | Campbell | A61B 5/029 |
| | | | | 600/526 |

(Continued)

FOREIGN PATENT DOCUMENTS

| | | |
|---|---|---|
| EP | 2452621 A1 | 5/2012 |
| EP | 2257217 B1 | 4/2017 |

(Continued)

*Primary Examiner* — Navin Natnithithadha
(74) *Attorney, Agent, or Firm* — McGlew and Tuttle, P.C.

(57) ABSTRACT

A medical device (100) determines a resistance parameter (107), of a patient to be treated, indicating a peripheral vascular resistance. A reception module (110) is configured to receive a pulsatile signal (112). The pulsatile signal indicates a blood pressure curve (114), especially an arterial blood pressure curve, or a blood volume curve. A reading module (120) is connected to the reception module and is configured to read a number of predefined curve parameters (124) from the received pulsatile signal and to provide corresponding, read measured values (134) for the number of predefined curve parameters. A calculation module (130) is connected to the reading module and is configured to calculate the resistance parameter of the patient with the use of a predefined estimation function (136) based on the read measured values and on a predefined parameter (135) indicating the cardiac output of the patient and to output same.

16 Claims, 5 Drawing Sheets

(56)          References Cited

U.S. PATENT DOCUMENTS

| | | | | |
|---|---|---|---|---|
| 2001/0016690 A1* | 8/2001 | Chio | ..................... | A61B 5/022 |
| | | | | 600/526 |
| 2006/0235323 A1* | 10/2006 | Hatib | .................. | A61B 5/0215 |
| | | | | 600/526 |
| 2008/0287812 A1 | 11/2008 | Parlikar et al. | | |
| 2011/0040195 A1* | 2/2011 | Knoll | .................... | A61B 5/029 |
| | | | | 600/485 |
| 2012/0259189 A1 | 10/2012 | Cohen et al. | | |
| 2014/0303509 A1* | 10/2014 | Campbell | ............. | A61B 8/488 |
| | | | | 600/485 |

FOREIGN PATENT DOCUMENTS

| | | | |
|---|---|---|---|
| EP | 3307146 | B1 | 11/2020 |
| JP | 2005253657 | A | 9/2005 |
| JP | 2008536545 | A | 9/2008 |
| JP | WO2017179701 | A1 | 2/2019 |

* cited by examiner

500

510

520

530

540

550

MEDICAL DEVICE FOR EVALUATING A PULSATILE SIGNAL

CROSS REFERENCE TO RELATED APPLICATIONS

This application claims the benefit of priority under 35 U.S.C. § 119 of German Application 10 2020 124 582.3, filed Sep. 22, 2020, the entire contents of which are incorporated herein by reference

TECHNICAL FIELD

The present invention pertains to a medical device for determining a resistance parameter of a patient to be treated, which said resistance parameter indicates the peripheral vascular resistance. Furthermore, the present invention pertains to a medical device and to a process for determining a resistance parameter indicating the peripheral vascular resistance, as well as to a computer program with a program code for carrying out such a process.

TECHNICAL BACKGROUND

It is known that in addition to the cardiac minute volute, the peripheral vascular resistance and the compliance of the arterial vascular system are important for the intensive care monitoring of a patient. Thus, these physiological variables make possible a rapid and reliable classification of states of shock in order to initiate a suitable therapy as quickly as possible. Furthermore, these are reliable parameters for an automated catecholamine therapy for stabilizing the blood pressure of the patient.

A process, in which the mean arterial blood pressure and a central venous blood pressure are determined in order to determine therefrom the peripheral vascular resistance, has become established in clinical practice for the determination of the peripheral vascular resistance.

SUMMARY

An object of the present invention is to provide an improved medical device for determining a resistance parameter indicating the peripheral vascular resistance, especially for the especially simple and rapid determination of this resistance parameter.

According to a first aspect of the present invention, a medical device is provided for determining a resistance parameter of a patient to be treated, which said resistance parameter indicates the peripheral vascular parameter, with a reception module, with a reading module and with a calculation module.

The reception module is configured to receive a pulsatile signal, wherein the pulsatile signal indicates a blood pressure curve, especially an arterial blood pressure curve, or a blood volume curve, measured especially as a photoplethysmogram, of the patient.

The reading module is connected to the reception module for signal technology and is configured to read a number of predefined curve parameters from the received pulsatile signal and to provide corresponding read measured values for the number of predefined curve parameters.

The calculation module is signal connected to the reading module (connected by signal technology) and is configured to calculate and to output the resistance parameter of the patient with the use of a predefined estimation function (predefined representation function), based on the read measured values and on a predefined parameter, the resistance parameter, which indicates the cardiac output of the patient.

It was found within the framework of the present invention that a non-invasive and yet reliable determination of the peripheral vascular resistance or of a resistance parameter indicating the peripheral vascular resistance is advantageous for an intensive medical care of a patient. The use of a predefined estimation function, which depends on characteristics of the received pulsatile signal and on the cardiac output or on a parameter indicating the cardiac output, is proposed for this according to the present invention.

Thus, the medical device according to the present invention makes possible a non-invasive determination of the peripheral vascular resistance and/or of the corresponding resistance parameter. Furthermore, the peripheral vascular resistance and/or the corresponding resistance parameter can be determined continuously during the treatment of the patient by the medical device according to the present invention.

The state of the patient can be monitored during the intensive care especially reliably according to the present invention due to the continuous determination. Thus, states of shock can be classified especially reliably or suitable for a transfer to a regular ward for the care of the patient can be recognized. The medical device according to the present invention thus makes it possible for the medical professional staff to respond especially rapidly and reliably to the current state of a patient in view to the measured pulsatile signal, e.g., of the blood pressure curve and/or of the blood volume curve.

Finally, the medical device according to the present invention makes possible an especially reliable determination of the peripheral vascular resistance and/or of the corresponding resistance parameter, especially an automated determination of these variables. The medical device can advantageously determine the desired variable without user inputs or at least with a small number of user inputs.

The medical device according to the present invention can be advantageously combined with prior-art target systems, e.g., with a ventilation system. Communication of the pulsatile signal with the medical device according to the present invention is not necessary for this.

The fact that a parameter indicates a variable in the sense of the present invention means that the variable in question can be directly inferred by the parameter. Thus, the resistance parameter indicates the peripheral vascular resistance of the patient, possibly by taking into account predefined constants and/or measured values. The parameter indicating the cardiac output is preferably the stroke volume, the cardiac minute volume, the stroke index and/or the cardiac index of the patient. These parameters make possible the determination of the cardiac output directly, possibly taking constants and/or measured values into consideration, and these parameters indicate the cardiac output in this sense. These parameters are especially relevant parameters for the analysis of the current state of the patient. These parameters are common medical parameters, whose medical relevance becomes immediately obvious to the professional. The stroke index of the heart is the existing cardiac output per square meter of body surface area of the patient. Furthermore, the cardiac index is the cardiac minute volume per square meter of body surface area of the patient. The cardiac minute volume is the quantity of blood that the heart pumps into the body of the patient during a certain time period, e.g., one minute. The cardiac output is the quantity of blood that the heart pumps into the body of the patient during a heartbeat. These variables thus correlate with the cardiac output and are therefore parameters indicating the cardiac output.

In the sense of the present invention, a pulsatile signal is a signal that indicates a measured value curve consisting of a plurality of pulses. The pulsatile signal received by the reception module indicates according to the present invention the blood pressure curve and/or the blood volume curve of the patient and hence a number of blood pressure pulses and/or blood volume pulses, especially of current blood pressure pulses and/or current blood volume pulses of the patient.

A signal connection (for signal technology) is a connection that allows the exchange of a signal. This connection may be a wireless connection or a cable-based connection. The modules of the medical device according to the present invention may be in this sense at least partially separate modules, which are separated from one another and are especially separated from one another in space. As an alternative or in addition, the modules of the medical device according to the present invention may be located at least partially within a common housing as a common component of the medical device. The different modules of the medical device are separated from one another according to the present invention at least at the software level as separate software blocks.

According to the present invention, the reception module may be an interface, which does not carry out any signal processing, but only forwards the received pulsatile signal to the reading module. As an alternative, the reception module may be configured to process the pulsatile signal, for example, to convert the pulsatile signal into a signal form which the reading module can process further.

Preferred embodiments of the medical device according to the present invention will be described below.

In an especially preferred embodiment, the number of predefined curve parameters is based on an end-diastolic state of a particular pulse of the pulsatile signal and/or on an end-systolic state of a particular pulse of the pulsatile signal. The end-systolic state is characterized in that it describes a point in the area of the so-called dicrotic notch within the curve of a blood pressure pulse or blood volume pulse. This dicrotic notch is formed within the course of a pulse due to the closure of the aortic valve of the heart and the drop in the blood pressure, which is associated with the closure. The systole ends and the so-called diastole begins at this time. No more blood flows out of the left ventricle of the heart into the aorta at this time, but the pressure built up in the elastic aorta during the systole continues to lead to a flow of blood volume in the vascular system of the systemic circulation of the patient. This point at the end of the systole, in the area of the dicrotic notch, is described in this case by the existing blood pressure or by the existing blood volume at the corresponding time. A blood pressure curve or blood volume curve is defined in this sense as a blood pressure curve or blood volume curve. The end-systolic state of a particular pulse is based in the sense of the present invention on the end-systolic blood pressure or blood volume in the area of the dicrotic notch.

In an advantageous variant of the above embodiment, the number of predefined curve parameters comprises at least one of the following curve parameters of a particular pulse: An end-systolic value; an end-diastolic value; a maximal value during a systole; a duration of a systole; and a duration of a diastole. A value is preferably defined in this case as a blood pressure or as a blood volume. This curve parameter is especially characteristic of the pulsatile signal and can therefore be read reliably. Furthermore, these predefined curve parameters make possible an especially rapid and reliable automatic reading of these variables for providing the read measured values for the calculation module. The analysis of a maximal value during the systole makes it possible to estimate (represent) the end-systolic value, which is typically at about 60% of the maximal value for blood pressure and blood volume. This is especially advantageous, for example, when a corresponding pressure sensor brings about a hyperattenuation of the signal, or if air bubbles have collected in the tube, as a result of which detection of the end-systolic value, i.e., for example, of the dicrotic notch, is especially difficult.

In the described variant of the embodiment, the predefined estimation function depends, especially linearly, for example, on a difference between the end-systolic value and the end-diastolic valve. The estimation function preferably depends on a difference between the end-systolic blood pressure and the end-diastolic blood pressure and/or on a difference between the end-systolic blood volume and the end-diastolic blood volume. Systematic inaccuracies in the determination of the predefined curve parameter can be removed from the result of the estimation function by the determination of the predefined curve parameter because only the difference between the two calculated values is incorporated in the result of the estimation function in the case of the difference. The resistance parameter of the patient can thus be determined in an especially robust manner against measurement errors.

In a preferred embodiment, the number of predefined curve parameters comprises a time constant of the pulsatile signal, which is determined on the basis of the curve of the pulsatile signal in the area of at least one diastole. Such a determination may be carried out, for example, by a logistic regression. Numerical methods for determining this variable from a time curve are known and will not therefore be explained below. The time constant as a predefined curve parameter can be determined numerically in an especially simple and reliable manner.

In an especially preferred variant of the above embodiment, the calculation module is further configured to calculate an arterial compliance of the patient on the basis of the resistance parameter of the patient and of the time constant and to output the arterial compliance of the patient. For example, the known physiological relationship that the time constant of the pulsatile signal is obtained from a product of the peripheral vascular resistance and the arterial compliance can be used for this. The arterial compliance represents the contribution of the elastic resistances of the arterial blood vessels to the resulting blood pressure. This variable is relevant for different known diagnostic methods, so that its determination is advantageous for the monitoring of a patient being treated in an intensive care unit.

The calculation module is further configured in another embodiment to calculate an estimated signal curve (representative signal curve) pertaining to the pulsatile signal on the basis of the resistance parameter and to output the estimated signal curve. For example, an estimated signal curve of the pressure can be calculated as a function of the arterial compliance and outputted for each heartbeat. This estimated signal curve is compared in a variant of this embodiment with the pulsatile signal, especially with the arterial blood pressure or with the received blood volume. Differences that are detected within the framework of this comparison can be outputted optically or acoustically, as a result of which an especially simple and robust implementation of an echocardiography is possible. The determination of the estimated signal curve is preferably likewise carried out on the basis of the predefined parameter indicating the cardiac output of the patient. An example of such an estimated signal curve is formed by a half sine wave function, whose starting point is set on the basis of the received pulsatile signal, whose amplitude is proportional to a quotient of the cardiac output and the arterial compliance, and whose period duration is obtained, in turn, from the duration of the systole and diastole from the pulsatile signal.

In an especially preferred embodiment, the predefined parameter indicating the cardiac output of the patient is predefined in a repeatedly updated manner and the calculation module is configured to use a correspondingly updated value for this parameter for the calculation of the resistance parameter. The respective updated value for the parameter is preferably received by the medical device and is outputted to the calculation module in order for this to replace the past value for the parameter by the updated value for the parameter. As a result, the calculated parameter indicating the cardiac output is especially reliable, because the values taken into consideration in the calculation were measured or determined currently in connection with the patient to be treated.

The medical device is configured in an especially advantageous variant of the above embodiment to calculate the updated value for the parameter indicating the cardiac output of the patient on the basis of the received pulsatile signal and of a predefined model rule. The pulsatile signal is preferably likewise analyzed in this case in respect to the predefined curve parameters, and the predefined curve parameters especially preferably pertain to an end-systolic value and to an end-diastolic value of a particular pulse of the pulsatile signal. An unambiguous assignment of the read curve parameters to the updated value for the parameter indicating the cardiac output of the patient, e.g., the cardiac output, the cardiac minute volume or the like, is then carried out on the basis of the predefined model rule. The medical device advantageously also determines in this variant, in addition to the resistance parameter, the parameter indicating the cardiac output. Since the cardiac output, the cardiac minute volume and the like are important parameters for the monitoring of a patient being treated in an intensive care unit, the medical device can advantageously determine a plurality of clinically relevant parameters from the received pulsatile signal.

For a conversion between cardiac output and stroke index or between cardiac minute volume and cardiac index, the medical device additionally has in one embodiment a patient monitoring module, which is configured to determine body metric characteristics of the patient and to estimate a body surface area of the patient therefrom. The output value for the calculated parameter indicating the cardiac output is processed in this case further based on the estimated body surface area of the patient, and it is processed further especially by means of the patient monitoring module on the basis of the estimated body surface area of the patient. The fact that the body surface area is taken into account by the patient monitoring module makes possible in this sense an especially reliable, patient-adapted analysis of the pulsatile signal, especially of the blood pressure curve and/or blood volume curve, by the medical device. Such additional information can improve the quality of the output of the medical device if the quality of the received pulsatile signal is so low that the analysis of the pulsatile signal via the reading module leads the calculation module to a comparatively inaccurate result. Furthermore, the patient monitoring module is advantageous above all when patients with an especially small or especially large body surface area are examined, because an analysis of the blood pressure curve or blood volume curve, which is not standardized on the basis of the body surface area, makes it possible to infer the physiological state of the patient only inaccurately. Body metric characteristics are, for example, an estimated abdominal volume, an estimated abdominal girth, an estimated height, an estimated arm length and/or an estimated span of the arms of the patient.

In an especially advantageous variant of the above embodiment, the patient monitoring module comprises an optical sensor system for detecting the body metric characteristics of the patient. A body surface area or at least a value indicative of the body surface area of the patient can be estimated on the basis of the body metric characteristics by means of such an optical sensor system, preferably by means of a camera system, in an automated procedure in an especially simple manner.

In one embodiment, which is an alternative to the above two embodiments, a constant estimated value (constant representative value) is used for the predefined parameter indicating the cardiac output of the patient. The resistance parameter can be determined hereby according to the present invention by the medical device in an especially simple manner and rapidly. In particular, no calculation or processing steps are necessary for the updating of the parameter indicating the cardiac output. For example, a simple non-invasive determination of high blood pressure can be made possible as a result according to the present invention, taking into account a known cross sensitivity to a change in the peripheral vascular resistance. In particular, the outputted resistance parameter can be used to support known diagnostic methods. Even though the assumption of a constant cardiac minute volume within the framework of this embodiment may lead to a limitation of the accuracy of the calculated parameter, it makes it also possible to use the medical device according to the present invention in simple mobile devices, e.g., in smart watches and/or blood pressure gauges.

According to a second aspect of the present invention, a medical system for determining a resistance parameter of a patient to be treated, which parameter indicates the peripheral vascular resistance, is proposed for accomplishing the above-mentioned object, wherein said medical system has a medical device according to at least one of the above embodiments and a measuring device, which is configured to measure a measured value curve of the patient, which curve indicates the blood pressure curve or the blood volume curve, and to make it available as a pulsatile signal.

The medical device within the medical system according to the present invention may be present in the same embodiments as the medical device according to the present invention and the medical system has as a result all the advantages that the corresponding embodiment of the medical device has as well.

Furthermore, the medical system according to the present invention makes it advantageously possible for the medical device and for the measuring device to be coordinated with one another for signal technology (signal coordinated). As a result, a simple analysis, especially a rapid analysis, of the pulsatile signal is possible in an especially advantageous manner.

In an especially preferred embodiment, the measuring device according to the present invention sends a quality indicator for the pulsatile signal together with the pulsatile signal. As a result, the medical device is capable of analyzing only the pulses of the indicated measured value curve in which the signal quality of the pulsatile signal is above a predefined threshold value.

In another preferred embodiment, the measuring device is configured to measure the blood pressure curve of the patient, wherein the pulsatile signal provided is a blood pressure signal. In an especially preferred variant of this embodiment, the measuring device is configured for the non-invasive measurement of the blood pressure curve of the patient. Such a non-invasive measurement can be carried out by means of one of the prior-art non-invasive processes, for example, a photoplethysmogram.

According to a third aspect of the present invention, a process for determining a resistance parameter indicating the peripheral vascular resistance of a patient to be treated is proposed for accomplishing the above-mentioned object, said process having the following steps:

receipt of a pulsatile signal, wherein the pulsatile signal indicates a blood pressure curve, especially an arterial blood pressure curve, or a blood volume curve of the patient;

reading of a number of predefined curve parameters from the received pulsatile signal;

provision of read measured values for the number of predefined curve parameters;

calculation of the resistance parameter of the patient with the use of a predefined estimation function based on the read measured values and on a predefined parameter indicating the cardiac output of the patient; and outputting of the resistance parameter.

The process according to the present invention can be carried out by the medical device according to the present invention, so that it may have different embodiments corresponding to the described embodiments of the medical device. It correspondingly has the same advantages as the respective described embodiments of the medical device.

The process steps according to the present invention are carried out in the order described. Thus, the pulsatile signal is always received first before the predefined curve parameters can be read from the pulsatile signal in order to calculate the resistance parameter of the patient based on it and to output it. In a preferred embodiment, all process steps are carried out one after another such that the output of the resistance parameter takes place essentially in real time. There preferably are less than 20 sec, especially less than 10 sec and preferably less than 5 sec between the receipt of the pulsatile signal and the output of the resistance parameter.

In another embodiment, the calculation and the outputting of the resistance parameter is triggered by a user input, which indicates a request for the resistance parameter. Such an input may be carried out, for example, via an input module of the medical device according to the present invention.

The process steps of the process according to the present invention are preferably carried out by a device, especially by a single processor. As an alternative, the process steps are carried out at least partially by different processors.

According to a fourth aspect of the present invention, a computer program with a program code for carrying out a process according to the third aspect of the present invention when the program code is executed on a computer, on a processor or on a programmable hardware component is proposed for accomplishing the above-mentioned object. A plurality of steps of the process according to the present invention are preferably carried out by a shared computer, by a shared processor or by a shared programmable hardware component. The individual steps are preferably separated in this case from one another at least at the software level by corresponding software blocks. All steps of the process according to the present invention are carried out especially preferably on a shared computer, on a shared processor or on a shared programmable hardware component.

The present invention shall be explained now in more detail on the basis of advantageous exemplary embodiments shown schematically in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
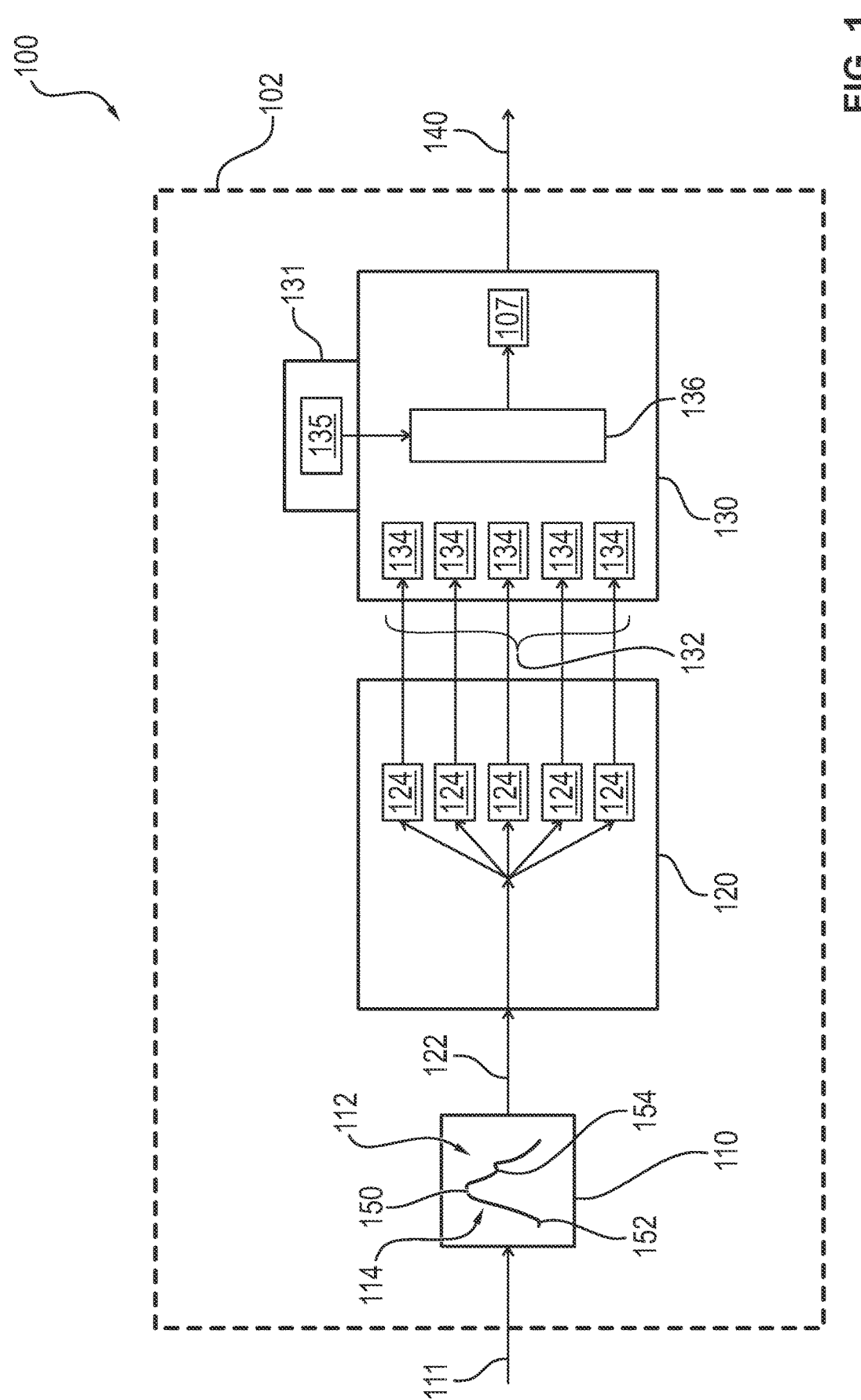
FIG. 1 is a schematic view of a first exemplary embodiment of a medical device according to a first aspect of the present invention.

Referring to the drawings, FIG. 1 shows a schematic view of a first exemplary embodiment of a medical device 100 according to a first aspect of the present invention.

The medical device 100 is configured to determine a resistance parameter 107 of a patient to be treated, which resistance parameter indicates the peripheral vascular resistance. It comprises for this purpose a reception module 110, a reading module 120 and a calculation module 130.

The reception module 110 is configured to receive a pulsatile signal 112, wherein the pulsatile signal 112 indicates a blood pressure curve 114, especially an arterial blood pressure curve, or a blood volume curve of the patient. The pulsatile signal 112 is always a typical blood pressure curve with a dicrotic notch at the end of a systole within the framework of the exemplary embodiments shown for the sake of simplicity. However, all explanations for the pulsatile signal 112 hold true analogously for a blood volume curve. The reception module 110 has a communication interface for the input data 111 with a pulsatile signal 112 contained therein for receiving the pulsatile signal 112. This communication interface is configured in the exemplary embodiment shown for the cable-based receipt of the input data 111 with the pulsatile signal 112. In one exemplary embodiment, not shown, the communication interface is configured for the wireless receipt of the pulsatile signal. The pulsatile signal 112 is converted by the reception module 110 into a signal format readable for the reading module 120. The reception module can output for this the pulsatile signal in an unchanged form to the reading module in a variant of this exemplary embodiment, because the reading module can already read the signal format received by the reception module.

The reading module 120 is connected to the reception module 110 for signal technology. The connection is a cable-based signal connection 122 in this case. In one exemplary embodiment, not shown, this connection has a wireless configuration. Furthermore, the reading module 120 is configured to read a number of predefined curve parameters 124, especially blood pressure curve parameters, from the received pulsatile signal 112 and to make correspondingly read measured values 134 available for the number of predefined curve parameters 124. These measured values 134 are outputted via a common measured value signal 132 to the calculation module 130. In an alternative exemplary embodiment, the measured values are outputted via separate signals to the calculation module.

The calculation module 130 is connected for signal technology to the reading module 120 for providing the measured value signal 132. This connection may be a cable-based or wireless connection. Furthermore, the calculation module 130 is configured to calculate the resistance parameter 107 of the patient with the use of a predefined estimation function (predetermined representation function) 136, based on the read measured values 134 and on a predefined parameter 135, the resistance parameter 107 of the patient, which indicates the cardiac output of the patient. The predefined estimation function 136 is stored in the calculation module 130. The estimation function 136 is not preferably changed any longer after a one-time entry into the memory, for example, during the manufacture of the medical device 100. The parameter 135 indicating the cardiac output of the patient is stored in a separate memory area 131 of the calculation module 130. In the exemplary embodiment shown, the stored parameter 135 is an estimated value maintained at a constant value, which is not changed at least during the treatment of a patient by the medical device 100. This estimated value, which is maintained at a constant value, is preferably not changed during the operation of the medical device 100. Exemplary embodiments that allow a change of this parameter 135 are shown, for example, in FIGS. 2, 3 and 4.

Finally, the calculation module 130 is also configured to output an output signal 140, which indicates the calculated resistance parameter 107. The output signal 140 is outputted in the exemplary embodiment shown to an external device, not shown, in a cable-based manner. In another exemplary embodiment, the output signal is outputted in a wireless manner. The medical device 100 has a communication interface, not shown, for this output. The interface may be, for example, a cable-based interface, e.g., a bus system, a USB interface or an Ethernet interface, or a wireless interface, for example, a WLAN, Bluetooth, ZigBee or BLE interface.

The number of predefined curve parameters 124 equals five in this case, and these parameters are based at least partly on an end-diastolic state 152 of a particular pulse 150 of the pulsatile signal 112 and/or on an end-systolic state 154 of the particular pulse 150 of the pulsatile signal 112. The curve parameters 124 thus comprise an end-systolic blood pressure, an end-diastolic blood pressure, a duration of a systole and a duration of a diastole. Moreover, the time constant of the pulsatile signal 112 is a predefined curve parameter 124, which is determined in the area of at least one diastole based on a logistic regression. Details of the numerical conversion of such a logistic regression are known to the person skilled in the art and will not therefore be explained below.

The following association of the curve parameters 124 with the resistance parameter 107 is used concretely as the estimation function 136 in the exemplary embodiment shown:

$$R_p = \frac{2 \cdot \sqrt{2}}{\pi} \cdot \frac{T_{sys}}{SV} \cdot \frac{1 - e^{-\frac{T_{sys} + T_{dia}}{\tau}}}{\left(1 - e^{-\frac{T_{sys}}{\tau}}\right) \cdot \left(1 - e^{-\frac{T_{dia}}{\tau}}\right)} \cdot (P_{a,es} - P_{a,ed})$$

With this estimation function, $R_p$ describes the peripheral vascular resistance of the patient, $T_{sys}$ the duration of a systole, $T_{dia}$ the duration of a diastole, $P_{a,es}$ the blood pressure at the end of a systole, $P_{a,ed}$ the blood pressure at the end of a diastole, SV the cardiac output of the patient and T the time constant of the received pulsatile signal. The calculated resistance parameter consequently depends linearly on a difference between an end-systolic value, namely, the end-systolic blood pressure, and on an end-diastolic value, namely, an end-diastolic blood pressure. In one variant, a plurality of pulses of the pulsatile signal are analyzed in order to calculate the resistance parameter, for example, on the basis of a mean value of at least one subset of the predefined parameters read in the process.

Other estimation functions are estimation functions according to the present invention precisely if they describe an association between a curve parameter and a parameter indicating the cardiac output with the resistance parameter of the patient. In particular, a product dependent on the time constant can be used instead of the e-function, for example, by a corresponding expansion of the e-function up to the first, second or third order. Consequently, the subject of the present invention is not limited to the use of the estimation function indicated or to similar estimation functions.

In the exemplary embodiment shown, all modules of the medical device 100 are arranged in a common housing 102 of the medical device 100. In particular, all modules are configured as a shared processor, not shown, wherein the modules are separated from one another at least at the software level.

The use of a permanently predefined parameter indicating the cardiac output corresponding to the exemplary embodiment described makes possible an especially simple and compact mode of construction of the medical device 100. In an especially advantageous exemplary embodiment, the medical device 100 is a smart watch, a mobile blood pressure gauge or a portable device for combined operation with another medical device, e.g., a ventilator or the like.

In one exemplary embodiment, not shown, the modules of the medical device are configured at least partially at spaced locations from one another and are configured by different hardware components.

Figure 2:
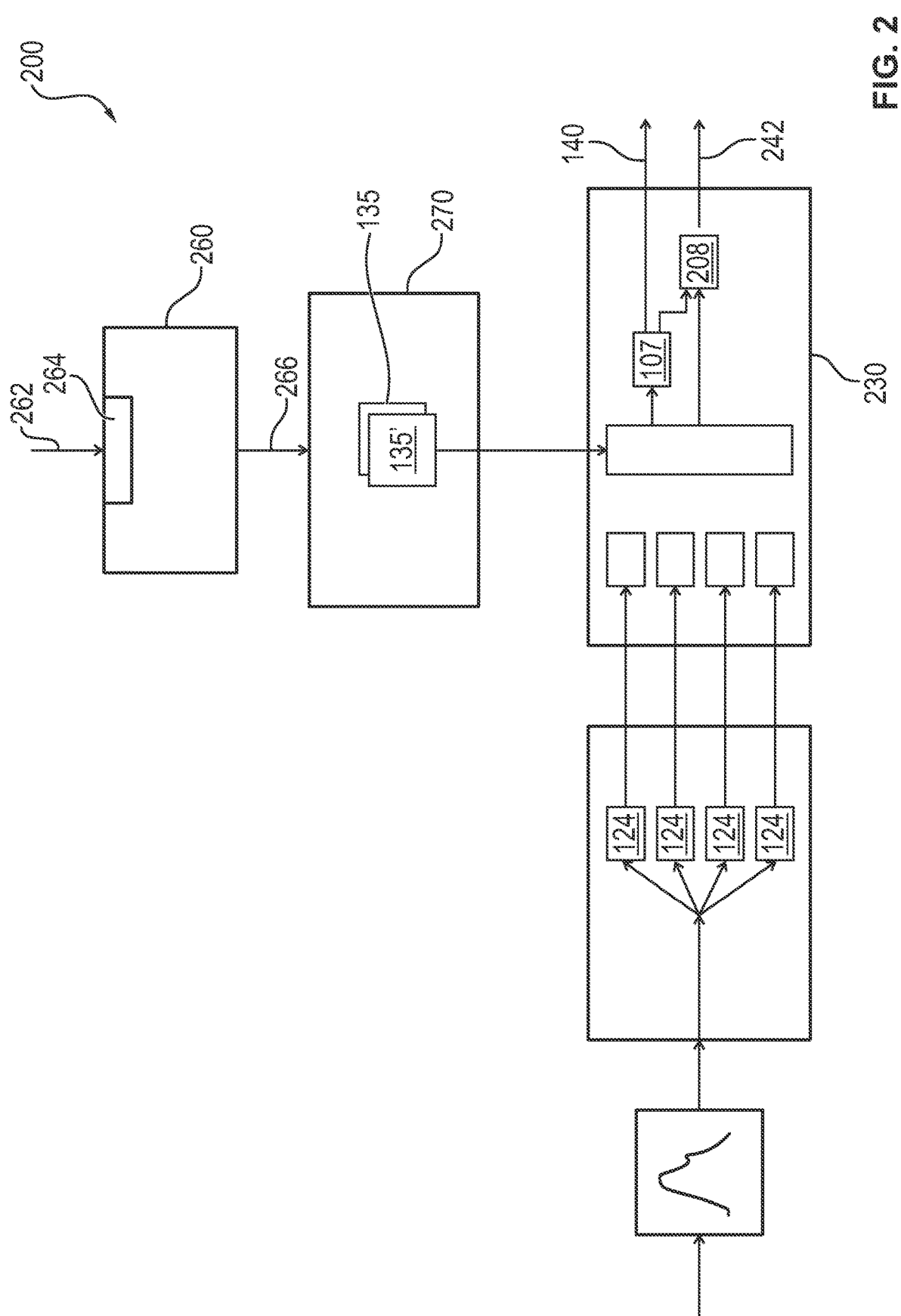
FIG. 2 is a schematic view of a second exemplary embodiment of the medical device according to the first aspect of the present invention.

FIG. 2 shows a schematic view of a second exemplary embodiment of the medical device 200 according to the first aspect of the present invention.

The medical device 200 differs from the medical device 100 shown in FIG. 1 in that the parameter 135 indicating the cardiac output is not a constant estimated value, but is predefined as a repeatedly updated value. The medical device 200 has for this purpose an input module 260, which is configured to receive a user input 262 via an input interface 264 and to provide corresponding input information 266. Furthermore, the medical device 200 comprises a separate memory module 270, in which the parameter 130 indicating the cardiac output is stored. The memory module 270 is configured to receive the input information 266 and to determine from the input information 266 an updated value 135' for the parameter indicating the cardiac output and to output it as a predefined parameter to the calculation module 230. The input interface 264 is preferably configured for a wireless communication with an external device, which provides the updated value 135' for the parameter 135 indicating the cardiac output. In one exemplary embodiment, not shown, the communication with the input interface takes place in a cable-based manner.

Furthermore, the medical device 200 differs from the medical device 100 in that only four different predefined curve parameters 124 are read and used for the calculation of the resistance parameter.

Finally, the medical device 200 also differs from the medical device 100 in that the calculation module is further configured to calculate an arterial compliance 208 of the patient on the basis of the resistance parameter 107 and of the time constant and to output it. The calculation of the arterial compliance 208 is carried out preferably by the time constant being divided by the arterial vascular resistance. The value for the arterial compliance is outputted in this case via a separate output signal 242, which differs from the output signal 140 for outputting the resistance parameter 107. In one exemplary embodiment, not shown, a plurality of output values, e.g., the arterial compliance and the arterial vascular resistance are outputted via a common output signal.

In one exemplary embodiment, not shown, the calculation module is further configured to calculate an estimated signal curve (a representative signal curve) pertaining to the pulsatile signal on the basis of the resistance parameter and to output the estimated signal curve. The estimated signal curve preferably pertains to a blood pressure curve or to a blood volume curve.

Figure 3:
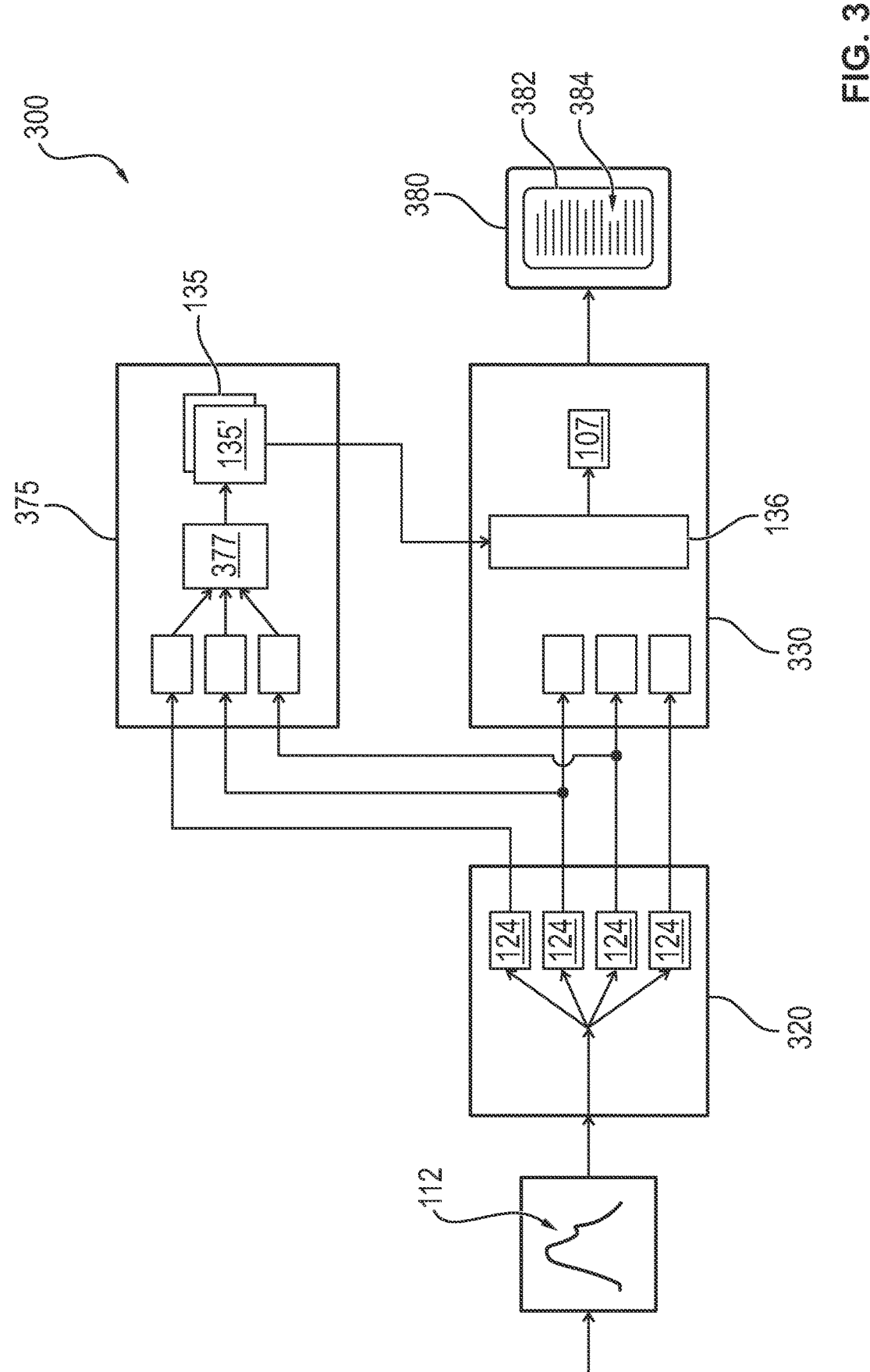

FIG. 3 shows a schematic view of a third exemplary embodiment of the medical device 300 according to the first aspect of the present invention.

The medical device 300 differs from the medical device 200 in that the updated value 135' for the parameter indicating the cardiac output is determined by a separate analysis module 375 of the medical device 300. Three predefined curve parameters 124 are transmitted for this from the reading module 320 to the analysis module 375. In addition, three predefined curve parameters 124 are transmitted from the reading module 320 to the calculation module 330, and a total of four different predefined curve parameters 124 are read by the reading module 320 from the pulsatile signal 112.

The determination of the cardiac output, especially the automated determination of the cardiac output or of a parameter indicating the cardiac output, is carried out on the basis of a predefined model rule 377, which describes how the predefined curve parameters are taken into account for this result of the analysis unit 375. Such a model rule is preferably based on calibration information or on data detected by the medical device in the past. Based on such a data set, such a model rule 377 can be determined by means of numerical processes, for example, by means of a multi-dimensional regression in a manner known to the person skilled in the art and can be made available for the processing by the analysis module 375. The updated value 135' is received, in turn, as a predefined parameter 135 indicating the cardiac output and is used for calculating the resistance parameter by means of the estimation function 136.

Furthermore, the medical device 300 differs from medical devices according to the above exemplary embodiments in that it has an output module 380, which provides via a display 384 a visual output, which indicates the resistance parameter 107 calculated according to the present invention.

In the exemplary embodiment shown, the output module 380 is a component of the medical device according to the present invention. In the exemplary embodiment shown in FIG. 4, the output module is a part of an external device, which is not comprised by the medical device.

Figure 4:
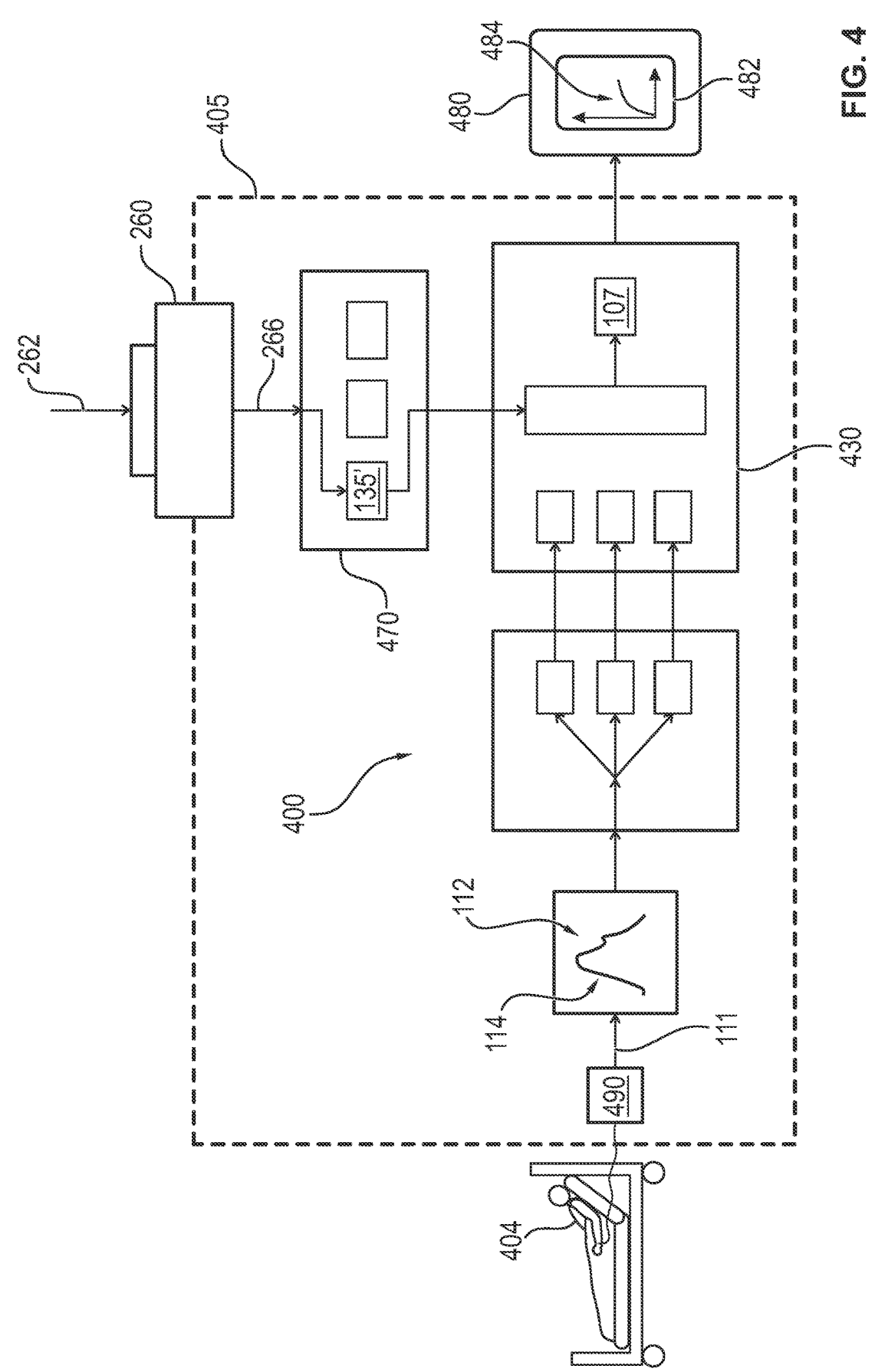
FIG. 4 is a schematic view of a third exemplary embodiment of the medical system according to the second aspect of the present invention.

FIG. 4 shows a schematic view of an exemplary embodiment of a medical system 405 according to a second aspect of the present invention.

The medical system 405 is configured to determine a resistance parameter 107 of a patient 404 to be treated, which resistance parameter indicates the peripheral vascular resistance. The medical system 405 comprises for this purpose the medical device 400 according to the first aspect of the present invention and a measuring device 490, which is configured to measure a measured value curve of the patient 404, which measured value curve indicates the blood pressure curve or the blood volume curve, and to make it available.

The measuring device 490 is configured in this case to measure the blood pressure curve 114 of the patient, wherein the input data 111 provided indicate the pulsatile signal 112 and make it thereby available for further processing. The indicated pulsatile signal is a blood pressure signal in this case. As an alternative or in addition, the pulsatile signal may comprise a blood volume signal. The measuring device 490 is configured in this case for the non-invasive measurement of the blood pressure curve 114 of the patient 404. Such a non-invasive measurement may be, for example, an optical measurement, an ultrasound-based measurement or a measurement by means of a pressure pickup. This is a photoplethysmograph, which is known to carry out an optical measurement, in the exemplary embodiment shown.

The medical device 400 within the measuring system 405 has, as was already shown in FIG. 2, an input module 260 for receiving a user input 262, which contains, in turn, input information 266. The input information 266 indicates in this case from a predefined number of predefined parameter values indicating the cardiac output the parameter value that is suitable for the current state of the patient 404. The user input 262 explicitly comprises for this purpose, for example, the value to be used for this parameter, classification information, which make possible an association with a predefined value for the parameter, or a selection of the parameter value from a predefined plurality of suitable values, which said selection is provided via a graphic user surface.

The separate memory module 470 is configured in the exemplary embodiment shown to distinguish between three different patient states and thereby to provide one of three parameter values as a currently predefined value for the parameter indicating the cardiac output. The user input is a wireless user input, which comprises a signal, which is provided by an external device and which indicates the state of the patient. The updated value 135' for the cardiac output is determined from the state of the patient, especially from ventilation information and/or EKG information, and is outputted to the calculation module 430. In one exemplary embodiment, not shown, different parameter values are stored in the memory module for different patient categories, especially for different age groups of the patient and/or for different disease groups of the patient.

Furthermore, the medical device 400 differs from the medical device 300 in that the output module 480 is an external device, which is not comprised by the medical system 405. The output module 480 is connected to the calculation module 430 in a cable-based or wireless manner. The output module 480 is connected in this case to the calculation module 430 in a cable-based or wireless manner and comprises a display 482 for outputting a visual output 484.

Figure 5:
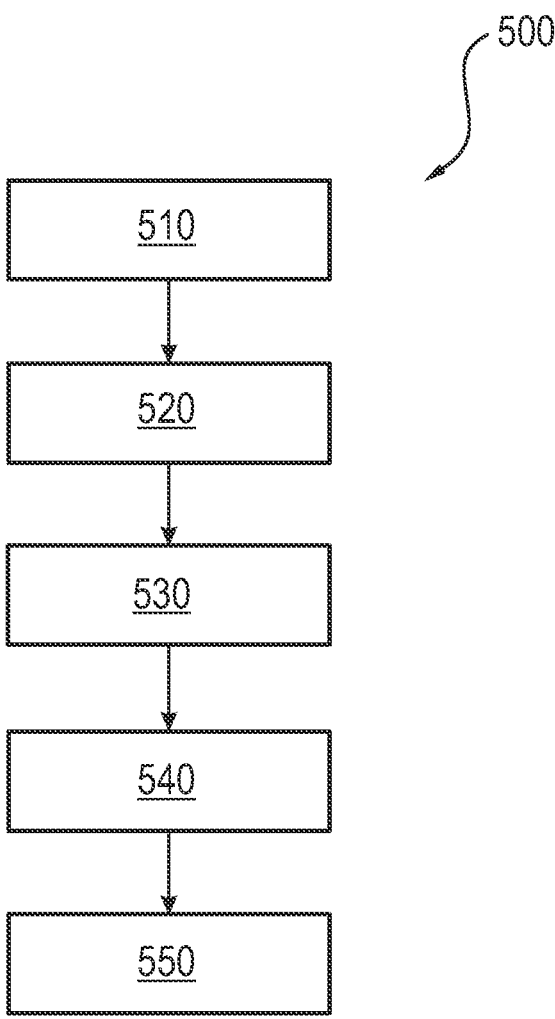
FIG. 5 is a flow chart of an exemplary embodiment of a process according to a third aspect of the present invention.

FIG. 5 shows a flow chart of an exemplary embodiment of a process 500 according to a third aspect of the present invention.

The process 500 according to the present invention is configured for determining a resistance parameter of a patient to be treated, which resistance parameter indicates the peripheral vascular resistance. It has the process steps described below for this purpose.

A first step 510 comprises a receipt of a pulsatile signal, wherein the pulsatile signal indicates a blood pressure curve, especially an arterial blood pressure curve or a blood volume curve of the patient.

A next step 520 comprises a reading of a number of predefined curve parameters from the received pulsatile signal.

A next step 530 comprises a provision of read measured values for the number of predefined curve parameters.

Another step 540 comprises a calculation of the resistance parameter of the patient with the use of a predefined estimation function, based on the read measured values and on a predefined parameter indicating the cardiac output of the patient.

A final step 550 comprises an output of the resistance parameter.

These steps 510 through 550 are preferably carried out in the order shown. Thus, after receipt of the pulsatile signal in step 510, the relevant information, namely, the predefined curve parameter, is read and provided from this pulsatile signal within the framework of steps 520 and 530 in order to make it possible thereby to calculate the resistance parameter of the patient and to output it within the framework of steps 540 and 550.

The entire process 500 according to the present invention is preferably carried out essentially in real time. Preferably less than 20 sec, especially less than 10 sec and especially preferably less than 5 sec elapse between the receipt of the pulsatile signal and the outputting of the resistance parameter.

In one embodiment, not shown, the calculation and the outputting of the resistance parameter take place corresponding to steps 540 and 550 only after the receipt of a user input, which indicates a calculation to be carried out and output of the resistance parameter.

In another exemplary embodiment, not shown, the process comprises the additional step of receiving the parameter indicating the cardiac output of the patient. In an alternative or additional exemplary embodiment, not shown, the process has the additional step of calculating and providing a current value for the parameter indicating the cardiac output of the patient based on an additional number of predefined curve parameters and on a predefined model rule.

All steps of the process according to the present invention are preferably carried out on a shared processor. As an alternative, one step or a plurality of steps of the process according to the present invention may be carried out at least partly on a separate hardware component, e.g., on a separate processor.

While specific embodiments of the invention have been shown and described in detail to illustrate the application of the principles of the invention, it will be understood that the invention may be embodied otherwise without departing from such principles.

LIST OF REFERENCE NUMBERS

100, 200, 300, 400 Medical device
102 Housing
107 Resistance parameter
110 Reception module
111 Input data
112 Pulsatile signal
114 Blood pressure curve
120, 320 Reading module
122 Signal connection
124 Predefined curve parameters
130, 230, 330, 430 Calculation module
131 Memory area
132 Measured value signal
134 Read measured values
135 Parameter indicating cardiac output
135' Updated parameter indicating cardiac output
136 Estimation function
140 Output signal
150 Pulse
152 End-diastolic state
154 End-systolic state
208 Arterial compliance
242 Separate output signal
260 Input module
262 User input
264 Input interface
266 Input information
270, 470 Memory module
375 Analysis module
377 Predefined model rule
380, 480 Output module
382, 482 Display
384, 484 Visual output
404 Patient
490 Measuring device
500 Process
510, 520, 530, 540, 550 Process steps

What is claimed is:

1. A medical device for determining a resistance parameter of a patient to be treated, which resistance parameter indicates a peripheral vascular resistance, the medical device comprising:

a reception module configured to receive a pulsatile signal, wherein the pulsatile signal indicates a blood pressure curve or a blood volume curve of the patient;

a reading module connected to the reception module, the reading module being configured to read a number of predefined curve parameters from the received pulsatile signal and to provide corresponding read measured values for the number of predefined curve parameters;

a calculation module connected to the reading module, the calculation module being configured to instantaneously calculate, in real time, the resistance parameter of the patient with the use of a predefined estimation function based on the read measured values and based on a predefined parameter indicating the cardiac output of the patient and being configured to output the resistance parameter, wherein the number of predefined curve parameters is based on an end-diastolic value of a particular pulse of the pulsatile signal and on an end-systolic value of the particular pulse of the pulsatile signal, wherein the predefined estimation function is a function of a difference between the end-systolic value and the end-diastolic value, wherein the number of predefined curve parameters comprises a time constant of the pulsatile signal, which is determined via a curve of the pulsatile signal in the area of at least one diastole, wherein the calculation module is further configured to calculate an arterial compliance of the patient based on the resistance parameter of the patient and based on the time constant and to output the calculated arterial compliance of the patient; and an output module or an interface module configured to provide the calculated arterial compliance.

2. A medical device in accordance with claim 1, wherein the number of predefined curve parameters comprises at least one of the following curve parameters of the particular pulse: a maximal value during a systole; a duration of a systole; and a duration of a diastole.

3. A medical device in accordance with claim 2, wherein the predefined estimation function depends on a difference between the end-systolic value and the end-diastolic value.

4. A medical device in accordance with at least claim 1, wherein the calculation module is further configured to calculate an estimated signal curve pertaining to the pulsatile signal based on the resistance parameter and to output the calculated estimated signal curve.

5. A medical device in accordance with at least claim 1, wherein the predefined parameter indicating the cardiac output of the patient is predefined and repeatedly updated and the calculation module is configured to use a correspondingly updated value for the predefined parameter indicating the cardiac output of the patient for the calculation of the resistance parameter.

6. A medical device in accordance with claim 5, wherein the calculation module is further configured to calculate the updated value for the parameter indicating the cardiac output based on the received pulsatile signal and on a predefined model rule.

7. A medical device in accordance with claim 1, wherein a constant estimated value is used for the predefined parameter indicating the cardiac output of the patient.

8. A medical device in accordance with claim 1, wherein the output module comprises a display, the output module receiving the resistance parameter as input, the display being configured to display the resistance parameter.

9. A medical system for determining a resistance parameter of a patient to be treated, which resistance parameter indicates a peripheral vascular resistance, the medical system comprising:

a measuring device configured to measure a measured value curve of the patient, which measured value curve indicates a blood pressure curve or the blood volume curve, and to provide the measured value curve as a pulsatile output signal; and a medical device for determining the resistance parameter of a patient to be treated, which resistance parameter indicates the peripheral vascular resistance, the medical device comprising:

a reception module configured to receive the pulsatile output signal;

a reading module connected to the reception module, the reading module being configured to read a number of predefined curve parameters from the received pulsatile output signal and to provide corresponding read measured values for a number of predefined curve parameters;

a calculation module connected to the reading module, the calculation module being configured to instantaneously calculate the resistance parameter of the patient, in real time, with the use of a predefined estimation function based on the read measured values and based on a predefined parameter indicating the cardiac output of the patient and being configured to output the resistance parameter, wherein the number of predefined curve parameters is based on an end-diastolic value of a particular pulse of the pulsatile signal and on an end-systolic value of the particular pulse of the pulsatile signal, wherein the predefined estimation function is a function of a difference between the end-systolic value and the end-diastolic value, wherein the number of predefined curve parameters comprises a time constant of the pulsatile signal, which is determined via a curve of the pulsatile signal in the area of at least one diastole, wherein the calculation module is further configured to calculate an arterial compliance of the patient based on the resistance parameter of the patient and based on the time constant and to output the calculated arterial compliance of the patient; and an output module or an interface module configured to provide the calculated arterial compliance.

10. A medical system in accordance with claim 9, wherein the measuring device is configured to measure the blood pressure curve of the patient, and wherein the pulsatile signal provided is a blood pressure signal.

11. A medical system in accordance with claim 10, wherein the measuring device is configured for the non-invasive measurement of the blood pressure curve of the patient.

12. A medical system in accordance with claim 9, wherein the number of predefined curve parameters is based on an end-diastolic state of the particular pulse of the pulsatile signal and/or on an end-systolic state of the particular pulse of the pulsatile signal.

13. A medical system in accordance with claim 12, wherein the number of predefined curve parameters comprises at least one of the following curve parameters of the particular pulse: a maximal value during a systole; a duration of a systole; and a duration of a diastole.

14. A medical system in accordance with claim 13, wherein the predefined estimation function depends on a difference between the end-systolic value and the end-diastolic value.

15. A process for determining a resistance parameter of a patient to be treated, which resistance parameter indicates a peripheral vascular resistance, the process comprising the steps of:

receiving a pulsatile signal, wherein the pulsatile signal indicates a blood pressure curve or a blood volume curve of the patient;

reading of a number of predefined curve parameters from the pulsatile signal received;

providing read measured values for a number of predefined curve parameters;

instantaneously calculating the resistance parameter of the patient, in real time, using a predefined estimation function, based on the read measured values and on a predefined parameter indicating a cardiac volume of the patient, wherein the number of predefined curve parameters is based on an end-diastolic value of a particular pulse of the pulsatile signal and on an end-systolic value of the particular pulse of the pulsatile signal, wherein the predefined estimation function is a function of a difference between the end-systolic value and the end-diastolic value, wherein the number of predefined curve parameters comprises a time constant of the pulsatile signal, which is determined via a curve of the pulsatile signal in the area of at least one diastole, wherein the calculation module is further configured to calculate an arterial compliance of the patient based on the resistance parameter of the patient and based on the time constant and to output the calculated arterial compliance of the patient;

outputting the resistance parameter; and providing the calculated arterial compliance via an output module or an interface module.

16. A process according to claim 15, wherein a computer program is provided with a program code for carrying out at least some of the process steps upon the program code being executed one a computer, on a processor or on a programmable hardware component, wherein the resistance parameter of the patient is continuously determined and the calculated arterial compliance is continuously updated via the output module or the interface module.

\* \* \* \* \*